United States Patent [19]
Gernon et al.

[11] Patent Number: 5,453,543
[45] Date of Patent: Sep. 26, 1995

[54] PROCESS FOR THE MANUFACTURE OF HIGH PURITY LINEAR $C_4 +$ ALKYL MERCAPTANS

[75] Inventors: Michael D. Gernon, Upper Providence; Stanley R. Sandler, Springfield, all of Pa.

[73] Assignee: Elf Atochem North America, Inc., Philadelphia, Pa.

[21] Appl. No.: 320,347

[22] Filed: Oct. 11, 1994

[51] Int. Cl.$^6$ .................................................. C07C 319/06
[52] U.S. Cl. .................................................. 568/70
[58] Field of Search .................................................. 568/70

[56] References Cited

U.S. PATENT DOCUMENTS

| | | | |
|---|---|---|---|
| 2,829,171 | 4/1958 | Doumani | 568/70 |
| 3,081,353 | 3/1963 | Forni | 568/70 |
| 4,005,149 | 1/1977 | Kubicek | 568/70 |
| 4,059,636 | 11/1977 | Kubicek | 568/70 |
| 4,313,006 | 1/1982 | Hager | 568/70 |
| 4,396,778 | 8/1983 | Hager | 568/70 |
| 5,283,369 | 2/1994 | Clark et al. | 568/70 |

OTHER PUBLICATIONS

Koshelev et al., "Catalytic Conv. of DMS to MM", React. Kin. Cat. Letters, vol. 27, No. 2, pp. 387–391 (1985).

Kirk–Othmer, Ency. of Chem. Tech., Third Edition, vol. 2, pp. 228–225 (1972).

Mashkin et al., "Kinetic Studies of MM Prod. from DMS and $H_2S$" React. Kin. Cat. Letters, vol. 46, No. 1, pp. 187–192 (1992).

Koshelev et al., "Stability of Catalysts in DMS Conversion in The Presence of $H_2S$", React. Kin. Cat. Letters, vol. 44, No. 2, pp. 367–373 (1991).

*Primary Examiner*—James H. Reamer

[57] ABSTRACT

Linear $C_4+$ alkyl mercaptans of high purity are prepared by the reaction of a di-linear($C_4+$) alkyl sulfide with hydrogen sulfide at elevated temperature in the presence of a specified transition alumina material.

18 Claims, No Drawings

PROCESS FOR THE MANUFACTURE OF HIGH PURITY LINEAR $C_4$ + ALKYL MERCAPTANS

BACKGROUND OF THE INVENTION

This invention relates to the sulfhydrolysis of di-linear ($C_4$–$C_{18}$) alkyl sulfides at elevated temperature in the presence of a specified transition alumina catalyst to produce high purity linear ($C_4$–$C_{18}$) alkyl mercaptan. More particularly, it relates to the reaction of a di-linear ($C_4$–$C_{18}$) alkyl sulfide (RSR) with hydrogen sulfide ($H_2S$) at a temperature preferably ranging from about 150° up to about 400° C. in the presence of a specified transition alumina, to produce, the corresponding alkyl mercaptan in high purity and good yield.

THE PRIOR ART

It is known that mercaptans with higher alkyl groups can be synthesized by reaction of the corresponding higher di-alkyl sulfides with $H_2S$ at elevated temperature in the presence of certain sulfactive catalysts. U.S. Pat. No. 4,005,149 discloses the preparation of mercaptans by the sulfhydrolytic cleavage of di-alkyl sulfides such as di-n-dodecyl sulfide and di-n-eicosyl sulfide, in the presence of alumina impregnated with cobalt molybdate. U.S. Pat. No. 4,396,778 discloses a vapor-phase process for preparing high purity $C_1$–$C_{18}$ alkyl mercaptans by reacting a dialkyl sulfide with an excess of $H_2S$ at elevated temperature in the presence of a specified zeolite.

A number of prior art references disclose the preparation of lower alkyl mercaptans, e.g. methyl mercaptan, by reacting the corresponding di-alkyl sulfides with $H_2S$ at elevated temperature in the presence of activated alumina. These references include U.S. Pat. Nos. 2,829,171 and 3,081,353, and technical articles in several issues of React. Kinet. Catal. Lett., authored by Koshelev et al., Vol. 27, No. 2, pp. 387–391 (1985); Vol. 44, No. 2, pp. 367–373 (1991); and Vol. 46, No. 1, pp. 187–192 (1992).

It has been shown that the contacting of $C_4$+ mercaptans and/or sulfides with a variety of catalysts including aluminas, at relatively high temperature produces variable amounts of 2-alkyltetrahydrothiophenes. This reaction is a dehydrocyclization, and can be described by the following equation:

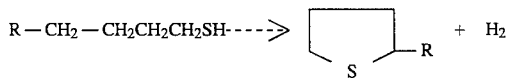

[Koshelev, supra, has published on this reaction in the open literature.]

Previous patents and publications involving the catalytic sulfhydrolyses of linear alkyl sulfides have not recognized nor reported the presence of 2-alkyltetrahydrothiophene by-products in their crude mercaptan product. These compounds (2-alkyltetrahydrothiophenes) can seriously impact on the economic viability of a sulfhydrolysis process in that it can be difficult to separate dehydrocyclized by-products from the derived mercaptan. In particular, the boiling point of a 2-alkyltetrahydrothiophene is oftentimes very close to the boiling point of the corresponding mercaptan. Reduction in the amount of impurities formed during a synthesis is always desirable, and the production of a high purity mercaptan by sulfhydrolyses absolutely requires a set of catalyst conditions which minimizes 2 - alkyltetrahydrothiophene formation.

SUMMARY OF THE INVENTION

This invention is a process for the preparation of high purity, linear alkyl mercaptan (RSH) having from 4 to 18 carbon atoms in the alkyl group comprising reacting a di-linear ($C_4$–$C_{18}$) alkyl sulfide (RSR) with hydrogen sulfide ($H_2S$) at elevated temperature in the presence of a catalytic material selected from the group consisting of an eta/gamma alumina, an eta/gamma alumina impregnated with up to 20 weight (wt.) percent of titania, an eta/gamma alumina impregnated with up to 20 weight (wt.) percent of rhenium oxide, and mixtures thereof.

DETAILED DESCRIPTION OF THE INVENTION

This invention concerns the synthesis of a high purity, linear ($C_4$–$C_{18}$) alkyl mercaptan (RSH) by reacting at elevated temperature a di-linear ($C_4$–$C_{18}$) alkyl sulfide (RSR) with hydrogen sulfide ($H_2S$) in the presence of a specified transition alumina catalyst.

The alkyl group of the sulfides and corresponding mercaptans of this invention include, for example, butyl, hexyl, octyl, nonyl, decyl, dodecyl, tetradecyl, hexadecyl and octadecyl, the foregoing being of linear structure.

The catalysts responsible for producing the unexpected results in this process are the gamma/eta alumina (transition aluminas rich in the gamma and eta phases), and such aluminas impregnated with up to 20 wt. % titania ($TiO_2$) or up to 20 wt.% of rhenium oxide ($Re_2O_7$). X-ray diffraction cannot distinguish between gamma and eta aluminas when both are present; accordingly, these phases are referred to as gamma/eta (eta/gamma) alumina unless the individual phase can be specifically identified by the method of preparation. The catalyst of this invention includes the individual phases of eta alumina and gamma alumina and reference to eta/gamma alumina includes each phase individually as well as a mixture of both. Commercial forms of eta/gamma alumina contain less than about 1 weight % of soda ($Na_2O$).

Transitional aluminas are discussed in the Kirk-Othmer Encyclopedia of Chemical Technology, Third Edition, Vol. 2, pp. 225–228. These materials are activated aluminas varying in crystal structure (or phases) depending on the method of preparation. They are identified by the form of their crystal structures and assigned names in accordance with Greek alphabet minor characters, i.e., gamma, delta, eta, theta, chi, kappa, iota and rho. The catalyst of the process of this invention is an alumina rich in the gamma/eta phases preferably with a reduced soda content, more preferably below 0.3 wt.%, most preferably below 0.1%, soda ($Na_2O$).

These transition aluminas may also be impregnated (e.g., by treatment with water solutions or dispersions and then drying), with titania or rhenium oxide to provide useful catalysts. The amount of oxide deposited on the alumina ranges up to 20% based on the weight of the combined catalyst material.

The catalysts are preferably employed in the process in the form of a fixed-bed, but may also be employed in any reactor or reaction form wherein the reactants contact or are contacted with the solid-catalytic material in an amount sufficient to beneficially effect the reaction.

In the preferred operation of the process, the catalyst is formed into small particulate objects, e.g., pelletized to a diameter or length and width of about 1/16–1/8 inch, and packed into the reactor to form a bed through which the reactants are passed in contact. The RSR reactant is generally passed through the reactor and in contact with the catalyst at a linear space velocity (LSV) ranging from about 0.1 to about 2.0, preferably 0.6 to 1.2 (LSV=grams of sulfide per gram catalyst-hour).

The temperature of the reaction is elevated and preferably ranges from about 150°0 to about 400° C., more preferably between 200° and 260° C. while the reaction pressure will preferably range from about 10 to 250 pounds per square inch (psi), more preferably from 40 to 150 psi. The reaction temperature may be controlled by heating the reactor to obtain the desired temperature in the catalyst bed. The reaction time is that sufficient to obtain the desired conversion and product purity. The reaction time is controlled, in a continuous reaction using a fixed-bed reactor, by the LSV employed as defined above.

The di-alkyl sulfide (RSR) starting material for the process may be obtained from any source. The degree of purity is not critical. Advantageously, one may use crude di-linear ($C_4+$) sulfides obtained as by-products in mercaptan-manufacturing processes, e.g., sulfide by-products of the reaction of alkenes or alcohols with $H_2S$. Such di-alkyl sulfide by-products are generally difficult or economically impractical to purify, and oftentimes these materials must be disposed of as chemical waste. The process of this invention is unexpectedly useful for the high yield conversion of di-linear ($C_4$–$C_{18}$) alkyl sulfides to the corresponding mercaptans with unprecedented low amounts of the thiophene dehydrocyclization impurity.

Hydrogen sulfide may be obtained as a by-product from a thiochemical reaction or a recycle from similar processes. Alternatively, the $H_2S$ may be a pure material manufactured as a process chemical. The $H_2S$ reactant is used in this process in amounts ranging from about 1 to about 20 moles $H_2S$ per mole of RSR.

Subsequent to the preparation of the mercaptan in the process of this invention, the crude mercaptan product is distilled to remove contaminants. Most by-products of the reaction are not problematic and, except for the dehydrocylcization impurity, they are easily removed from the mercaptan by distillation.

The unique feature of this invention is that the use of a transition alumina catalyst high in eta/gamma phases gives simultaneously both a high conversion to mercaptan and a very low conversion to the cyclized by-product (2-alkyltetrahydrothiophene). The eta/gamma alumina should preferably be low in ($Na_2O$) soda content, preferably below 0.3 wt.% Other transition alumina catalysts give a higher amount of cyclized by-product, especially at higher conversions to mercaptans (RSH).

EXAMPLES

Several experiments are reported hereinafter which exemplify the efficacy of the invention, or for comparative purposes. The experimental apparatus employed consisted of a one inch internal diameter stainless steel column approximately eighteen inches in length having means for sealing the ends, delivery ports at one end for the reactants under pressure, and an exit port at the other end for collecting the product. The column was packed with a first section of glass (inert) spheres, a central section of particulate catalyst and an end section of glass spheres. The catalyst charge may vary in size. The column was heated in a tube furnace and temperatures in the central catalyst bed were monitored by thermocouples running through the center of the steel reactor column. Pressure in the reactor was monitored by means of a thin-film pressure sensing transducer. RSR was pumped through the column and over the catalyst at a preset LSV (reported in grams sulfide per gram catalyst-hour). $H_2S$ was pumped through the reactor column at flow rates sufficient to provide a molar ratio of $H_2S$ to RSR of from 1:1 to 20:1. The parameters, i.e., sulfide LSV, pressure, temperature and $H_2S$/RSR molar ratio could all be independently varied.

A sample of "waste" RSR was obtained from a commercial mercaptan plant engaged in the manufacture of mercaptan from olefin (octene) and $H_2S$, and had the following composition:

| Components | wt. % |
| --- | --- |
| di-n-octyl sulfide | 86 |
| n-octyl, sec-octyl sulfide | 7 |
| other (octene, dioctyl disulfide, etc.) | 7 |

Equal portions of the above-described sample were used in comparative experiments employing various prior art catalysts and a catalyst of this invention. The results and parameters for the sulfhydrolysis processes are given in the following table. In each experiment, the temperature of the catalyst bed was maintained at 260° C., the pressure in the reactor was kept at 100 psi, and the molar ratio of $H_2S$ to RSR fed to the reactor was to 1.

| Exp. No. | Catalyst | % n-RSH | % Efficiency | % 2-BTHT* |
| --- | --- | --- | --- | --- |
| 1. | Co/Mo[a] | 20 | 20 | 5 |
| 2. | Ni/W[b] | 25 | 45 | 1 |
| 3. | Zeolite LZ-Y54[c] | 42 | 60 | 1.5 |
| 4. | Zeolite LZ-Y64[d] | 52 | 85 | 1.5 |
| 5. | Zeolite LZ-Y74[e] | 45 | 60 | 2.2 |
| 6. | Zeolite LZ-Y84[f] | 40 | 60 | 2.2 |
| 7. | MORDINITE[g] | 52 | 85 | 1.0 |
| 8. | ALUMINA (5% $K_2O$)[h] | 4 | 50 | 0.05 |
| 9. | ALUMINA (0.3% $Na_2O$)[i] | 15 | 80 | 0.02 |
| 10. | ALUMINA (<0.1% $Na_2O$)[j] | 55 | 85 | 0.02 |

[a]5% Cobalt oxide/16% Molybdenum Oxide on eta/gamma Alumina.
[b]5% Nickel oxide/20% Tungsten Trioxide on eta/gamma Alumina
[c]Y-type Synthetic Zeolite with 10% Soda
[d]Y-type Synthetic Zeolite with 2% Soda
[e]Y-type Synthetic Zeolite with 2% Soda hydrothermally stabilized.
[f]Y-type Synthetic Zeolite with 0.1% Soda
[g]Natural (mineral) Zeolite containing 0.1% Soda
[h]Specially Produced eta/gamma Alumina containing High (5%) $K_2O$
[i]Mined Alumina containing 0.3% Soda
[j]Eta/gamma Alumina with less than 0.1% Soda
*2-Butyl-tetrahydrothiophene
Catalyst Producers
a) Acreon
b) Engelhard
c)–g) UOP
h) Alcoa
i)–j) Engelhard The percent efficiency reported in the above table is calculated as, percent mercaptan produced, divided by the theoretical amount of mercaptan able to be produced, times 100. The percent mercaptan produced is determined by the weight percent of mercaptan found in the crude product following one pass of reactants through the reactor at an LSV of 1.0. The phase structure of the various alumina catalysts was determined by x-ray diffraction (XRD) analysis.

It is evident from a review of the data of the above table that the catalyst of the process of this invention is unexpectedly superior to those other catalysts of the prior art taught to be useful for the sulfhydrolysis of higher alkyl sulfides to form mercaptans. The high conversion rate and efficiency of product obtained coupled with the low production of the codistillable impurity (not recognized as a problem in the prior art) demonstrates the unique ability of the eta/gamma aluminas to effectively catalyze the sulfhydrolysis reaction with di-linear ($C_4$+) alkyl sulfides while simultaneously avoiding the production of large amounts of dehydrocyclization by-product.

Additional experiments for the process of this invention employing the catalysts of this invention, are disclosed in the following examples. The reactor apparatus employed for these experiments is that reported for the aforementioned comparative experiments. The "waste" RSR used in these examples was also obtained from a commercial mercaptan plant. It consisted of 86% di-n-octyl sulfide, 8% n-octyl, sec.-octyl sulfide and 6% other (octene, dioctyl disulfide, etc.)

EXAMPLE 1

A catalyst composed of pure alumina (gamma/eta phase) with less than 0.1% soda content was fashioned into a 1/16" extrudate cut to 1/8" lengths. The catalyst particles were packed by gravity into a one inch I.D. stainless steel tubular reactor. A catalyst charge of about 20 g. was used. The steel reactor tube was heated in a tube furnace until the catalyst bed reached the operating temperature. A sample of di-octyl sulfide "waste" was pumped through the heated tube at an LSV of 1.0 (1 g sulfide/g catalyst-hour). Hydrogen sulfide was allowed to flow through the tube at approximately 350 standard cubic centimeters per minute (sccm) (enough to obtain a 10/1 molar excess of $H_2S$ relative to RSR). The crude product was collected in a stainless steel sample vessel. The composition of the product stream exiting from the reactor was monitored by gas chromatography (GC) equipped with a flame ionization detector (FID). The following results show the effect of reaction temperature on the composition of the product obtained.

| Temperature (°C.)[1] | n-Octyl Mercaptan | % 2-BTHT[2] |
|---|---|---|
| 200 | 10 | 0.02 |
| 270 | 60 | 0.05 |
| 300 | 45 | 0.80 |

[1]The temperature was monitored by thermocouples in a thermowell which ran through the length of the reactor tube.
[2]The acronym "2-BTHT" is for 2-butyl-tetrahydrothiophene (dehydrocyclization by-product). The percentage is calculated based on n-alkyl mercaptan. ([% 2-BTHT/% n-RSH] × 100).

EXAMPLE 2

A catalyst composed of a alumina (gamma/eta phase) with approximately 5% soda content was fashioned into a 1/16 inch extrudate and cut at 1/8" lengths. As in Example 1, catalyst was packed by gravity into a one inch I.D. stainless steel tubular reactor. A catalyst charge of about 20 g was used. The steel reactor tube was heated in a tube furnace until the catalyst bed reached the desired operating temperature. A sample of di-octyl sulfide "waste" was pumped through the heated tube at an LSV of 1.0. Hydrogen sulfide was allowed to flow through the tube at approximately 350 sccm. The crude product was collected in a stainless steel sample vessel, and the composition of the product stream was monitored using GC (FID) as a function of temperature.

| Temperature (°C.) | % n-Octyl Mercaptan | % 2-BTHT |
|---|---|---|
| 260 | 7 | 0.01 |
| 320 | 22 | 0.50 |

EXAMPLE 3

A catalyst composed of eta/gamma alumina modified with 15% $TiO_2$ was fashioned into a 1/16" extrudate and cut at 1/8" lengths. As in Example 1, the catalyst was packed by gravity into a one inch I.D. stainless steel tube reactor. A catalyst charge of about 20 g was used. The steel reactor tube was heated in a tube furnace until the catalyst bed reached the desired operating temperature. A sample of di-octyl sulfide "waste" was pumped through the heated tube at an LSV of 1.0. Hydrogen sulfide was allowed to flow through the tube at approximately 350 sccm. The crude product was collected in a stainless steel sample vessel, and the composition of the product stream was monitored by GC(FID) as a function of temperature.

| Temperature (°C.) | % n-Octyl Mercaptan | % 2-BTHT |
|---|---|---|
| 210 | 8 | 0.05 |
| 240 | 16 | 0.10 |
| 290 | 60 | 0.15 |

Example 4

A catalyst composed of 10% Re (VII) (rhenium oxide) on eta/gamma alumina was fashioned into a 1/16" extrudate and cut to 1/8" lengths. As in Example 1, the catalyst charge of about 20 g was packed by gravity into a one inch I.D. stainless steel tubular reactor. The steel tube was heated in a tube furnace until the catalyst bed reached the desired operating temperature. A sample of di-octyl sulfide "waste" was pumped through the heated tube at an LSV of 1.0. Hydrogen sulfide was allowed to flow through the tube at approximately 350 sccm. The crude product was collected in a stainless steel sample vessel, and the composition of the product stream was monitored by GC (FID) as a function of temperature.

| Temperature (°C.) | % n-Octyl Mercaptan | % 2-BTHT |
|---|---|---|
| 200 | 10 | 0.1 |
| 220 | 18 | 0.2 |
| 260 | 42 | 0.2 |

EXAMPLE 5 .(Comparative)

A catalyst, composed of CoO (5%) and $MoO_3$ (16%) on eta/gamma alumina, was fashioned into a 1/16" extrudate and cut to 1/8" lengths. As in Example 1, the catalyst was packed by gravity into a one inch I.D. stainless steel tubular reactor. A catalyst charge of about 20 g was used. The steel reactor tube was heated in a tube furnace until the catalyst bed reached the desired operating temperature. A sample of di-octyl sulfide "waste" was pumped through the heated tube at a linear space velocity of 1.0. Hydrogen sulfide was allowed to flow through the tube at approximately 350 sccm. The crude product was collected in a stainless steel sample vessel, and the composition of the product stream was monitored by GC (FID) as a function of temperature.

| Temperature (°C.) | % n-Octyl Mercaptan | % 2-BTHT |
|---|---|---|
| 190 | 10 | 0.2 |
| 250 | 30 | 1.2 |
| 270 | 8 | 8.8 |

The data from Example 5 indicates the high level of % 2 BTHT obtained among CoO and $MoO_3$.

EXAMPLE 6

A catalyst composed of alumina rich in gamma/eta phase with soda content less than 0.1% was fashioned into a 1/16" extrudate and cut into 1/8" lengths. As in Example 1, the catalyst was packed by gravity into a one inch I.D. stainless steel tubular reactor. A catalyst charge of about 20 g was used. The steel reactor tube was heated in a tube furnace until the catalyst bed reached a temperature of 270° C. A sample of di-octyl sulfide "waste" was pumped through the heated tube at an LSV of 1.0. Hydrogen sulfide was allowed to flow through the tube at approximately 350 sccm. The crude product was collected in a stainless steel sample vessel. Crude product was sampled and analyzed by GC with a flame ionization detector at least twice in every 24 hour period. The crude product was consistently composed of 60% n-octyl mercaptan, 4% olefins (mostly octenes), 26% residual sulfide, and only 0.02% 2-butyltetrahydrothiophene (dehydrocyclization product). The catalyst showed no sign of diminished activity in a two week continuous trial.

We claim:

1. A process for the preparation of high purity, linear ($C_4$–$C_{18}$) alkyl mercaptan comprising reacting a di-linear ($C_4$–$C_{18}$) alkyl sulfide with hydrogen sulfide at elevated temperature in the presence of a catalytic amount of a material selected from the group consisting of an eta/gamma alumina, an eta/gamma alumina impregnated with up to 20 weight percent of titania, an eta/gamma alumina impregnated with up to 20 weight percent of rhenium oxide, and mixtures thereof.

2. The process of claim 1 wherein the catalytic material is solely an eta/gamma alumina.

3. The process of claim 2 wherein the eta/gamma alumina contains less than 0.3 weight percent $Na_2O$.

4. The process of claim 1 wherein the catalytic material is an eta/gamma alumina impregnated with up to weight percent titania.

5. The process of claim 1 wherein the catalytic material is a an eta/gamma alumina impregnated with up to 20 weight rhenium oxide.

6. The process of claim 1 wherein the elevated temperature ranges from about 150° to about 400° C.

7. The process of claim 1 wherein the pressure of the reaction ranges from about 10 to 250 psi.

8. The process of claim 1 wherein the reaction is carried out by continuously passing the reactants over a catalyst bed at a di-alkyl sulfide linear space velocity ranging from about 0.1 to about 2.0.

9. The process of claim 1 wherein hydrogen sulfide is reacted with the di-alkyl sulfide at a mole ratio of from 1:1 to 20:1.

10. A process for the preparation of high purity, linear ($C_4$–$C_{18}$) alkyl mercaptan comprising reacting a di-linear ($C_4$–$C_{18}$) alkyl sulfide with hydrogen sulfide at a temperature ranging from about 150° to about 400° C., at a pressure ranging from about 10 to about 250 psi, and in the presence of a catalytic amount of a material selected from the group consisting of an eta/gamma alumina, an eta/gamma alumina impregnated with up to 20 weight percent titania, an eta/gamma alumina impregnated with up to 20 weight percent rhenium oxide, and mixtures thereof.

11. The process of claim 10 wherein the reaction is carried out by continuously passing the reactants over a catalyst bed at a di-alkyl sulfide linear space velocity ranging from about 0.1 to about 2.0.

12. The process of claim 11 wherein hydrogen sulfide is reacted with the di-alkyl sulfide at a mole ratio of from 1:1 to 20:1.

13. The process of claim 12 wherein the catalyst is solely eta/gamma alumina.

14. The process of claim 12 wherein the catalyst is an eta/gamma alumina impregnated with titania.

15. The process of claim 12 wherein the catalyst is an eta/gamma alumina impregnated with rhenium oxide.

16. A process for the preparation of high purity, linear ($C_4$–$C_{18}$) alkyl mercaptan comprising reacting a di-linear ($C_4$–$C_{18}$) alkyl sulfide with hydrogen sulfide by passing the reactants at a hydrogen sulfide to di-alkyl sulfide mole ratio of from 6:1 to 12:1 and at a di-alkyl sulfide linear space velocity of from 0.6 to 1.2, over a catalytic amount of an eta/gamma alumina containing less than 0.3 weight percent soda ($Na_2O$) at a reaction temperature ranging from 200° to 260° C. and a reactor pressure ranging from 40 to 150 psi.

17. The process of claim 16 wherein the eta/gamma alumina contains less than 0.1 weight percent soda ($Na_2O$).

18. The process of claim 17 wherein the di-($C_4$–$C_{18}$) alkyl sulfide is di-n-octyl sulfide.

* * * * *

UNITED STATES PATENT AND TRADEMARK OFFICE
CERTIFICATE OF CORRECTION

PATENT NO. : 5,453,543
DATED : September 26, 1995
INVENTOR(S) : Gernon, Michael D. et al It is certified that error appears in the above-indentified patent and that said Letters Patent is hereby corrected as shown below:

Column 7, line 54, insert —20— after "to".

Signed and Sealed this

Twenty-eighth Day of November 1995

Attest:

BRUCE LEHMAN

Attesting Officer      Commissioner of Patents and Trademarks